(12) United States Patent
Anderson (10) Patent No.: US 7,998,146 B2
(45) Date of Patent: Aug. 16, 2011

(54) APPARATUS AND METHOD FOR HIP CUP EXTRACTION

(75) Inventor: James Anderson, Savannah, GA (US)

(73) Assignee: Innomed, Inc., Savannah, GA (US)

( * ) Notice: Subject to any disclaimer, the term of this patent is extended or adjusted under 35 U.S.C. 154(b) by 685 days.

(21) Appl. No.: 11/673,627

(22) Filed: Feb. 12, 2007

(65) Prior Publication Data

US 2008/0195111 A1    Aug. 14, 2008

(51) Int. Cl.
*A61B 17/58*   (2006.01)
*A61B 17/60*   (2006.01)
*A61F 2/00*    (2006.01)

(52) U.S. Cl. .......................................... 606/99; 606/91

(58) Field of Classification Search ............... 606/81, 606/82, 86, 91, 99, 99 R; 623/22.21, 21, 623/19, 18
See application file for complete search history.

(56) References Cited

U.S. PATENT DOCUMENTS

| | | | | |
|---|---|---|---|---|
| 4,528,980 | A | * | 7/1985 | Kenna .............................. 606/80 |
| 4,896,663 | A | * | 1/1990 | Vandewalls ..................... 606/79 |
| 5,370,704 | A | * | 12/1994 | DeCarlo, Jr. ................ 623/22.22 |
| 5,904,688 | A | * | 5/1999 | Gilbert et al. ............... 606/86 R |
| 6,063,124 | A | * | 5/2000 | Amstutz .................... 623/22.21 |
| 6,676,706 | B1 | | 1/2004 | Mears et al. |
| 6,953,480 | B2 | | 10/2005 | Mears et al. |
| 2002/0116007 | A1 | * | 8/2002 | Lewis ............................ 606/99 |

OTHER PUBLICATIONS

Sales brochure, Innomed, "Universal Hip Cup Removal System", 2006.

* cited by examiner

*Primary Examiner* — Thomas C Barrett
*Assistant Examiner* — Sameh Boles
(74) *Attorney, Agent, or Firm* — Philip H. Burrus, IV (57) ABSTRACT

A hip cup extraction apparatus (101) comprising a shaft (402), a handle (404), a semicircular cutting blade (406), a spring loaded latching member (408), and a head (100) for removing a hip cup (405) from a pelvic bone (401). The head (100) includes a semispherical section (102) terminating in a substantially planar surface (104), a hip cup extraction apparatus aperture (106), a retaining sleeve (108), and a three sided void (110). The head (100) may be configured for selective attachment to the hip cup extraction apparatus (101). The hip cup extraction apparatus (101) is inserted into the hip cup extraction apparatus aperture (106), and an optional spring loaded latching member (408) retains the head (100) in place. As the head (100) is being attached to the hip cup extraction apparatus (101), the semicircular cutting blade (406) may pass through the three sided void (110). Once the head (100) is attached to the hip cup extraction apparatus (101), the head (100) is inserted into the hip cup (405). Force may then be applied to the hip cup extraction apparatus (101) in order to drive the semicircular cutting blade (406) into the pelvic bone (401). The hip cup extraction apparatus (101) may then be rotated or pivoted such that the semicircular cutting blade (406) passes completely around the hip cup (405).

19 Claims, 7 Drawing Sheets

| Embodiment # | 1 | 2 | 3 | 4 | 5 | 6 | 7 | 8 | 9 | 10 |
|---|---|---|---|---|---|---|---|---|---|---|
| Spherical Section Diameter | 39 mm | 40 mm | 41 mm | 42 mm | 43 mm | 44 mm | 45 mm | 46 mm | 47 mm | 48 mm |
| Head Distal Length | 36 mm | 36.5 mm | 37 mm | 37.5 mm | 38 mm | 38.5 mm | 39 mm | 39.5 mm | 40 mm | 40.5 mm |

| Embodiment # | 11 | 12 | 13 | 14 | 15 | 16 | 17 | 18 | 19 | 20 |
|---|---|---|---|---|---|---|---|---|---|---|
| Spherical Section Diameter | 49 mm | 50 mm | 51 mm | 52 mm | 53 mm | 54 mm | 55 mm | 56 mm | 57 mm | 58 mm |
| Head Distal Length | 41 mm | 41.5 mm | 42 mm | 42.5 mm | 43 mm | 43.5 mm | 44 mm | 44.5 mm | 45 mm | 45.5 mm |

| Embodiment # | 21 | 22 |
|---|---|---|
| Spherical Section Diameter | 59 mm | 60 mm |
| Head Distal Length | 46 mm | 46.5 mm |

APPARATUS AND METHOD FOR HIP CUP EXTRACTION

BACKGROUND

1. Technical Field

This invention relates generally to an apparatus and method for removing a prosthetic hip cup from a pelvic bone, and more specifically to a tool having interchangeable heads for removing hip cups having different dimensions.

2. Background Art

Over the years, advances in medical procedures have helped countless people live normal lives after suffering devastating ailments. One such area of advancement has been in the field of orthopedic medicine, which is the curing of disorders of the musculoskeletal system. In particular, progress in the field hip replacement has been very important to helping those with mobility problems caused by hip damage.

One common type of hip ailment is the loss of cartilage in the hip sockets, which hold rotary balls attached to the femur bones. This relationship between the hip sockets and the rotary balls enables a person to walk and perform other movement of the legs. In a healthy hip, the cartilage present in the hip socket acts as a cushion that enables the rotary ball to move freely in the hip socket. As this cartilage deteriorates, sometimes with age and sometimes with disease, the rotary ball may begin to rub against the bone surface of the hip socket thereby causing bone on bone grinding. This grinding may be very painful.

To help people with damaged cartilage in their hips, doctors sometimes replace the rotary ball of the femur with a prosthetic rotary device, and insert a prosthetic hip cup into the pelvic bone. The prosthetic rotary device then fits within the prosthetic hip cup, and works as an artificial hip. Over time, these prosthetic pieces may become worn and may need to be replaced. Tools to replace the prosthetic hip cup are known in the art. The problem with these prior art replacement tools, however, is that they are typically designed for only one type or size of hip cup. For instance, they may be designed to work with only one manufacturer's cup or one size cup.

In recent years, new hip cup designs have been introduced. In general, these designs are made by different manufacturers and in different sizes. Because of their varying sizes, tools used to replace the specific hip cups are not suitable for use with these varying sized cup implants. For example, when a tool designed to remove the small hip cup is used to remove a larger hip cup, the tool may not seat properly within the cup, thereby making the cutting process erratic and haphazard.

There is thus a need for an improved hip cup removal device suitable for use with hip cups of varying sizes.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Before describing in detail embodiments that are in accordance with the present invention, it should be observed that the embodiments reside primarily in combinations of method steps and apparatus components related to an apparatus and method for employing a hip cup removal apparatus using a detachable head for removing a prosthetic hip cup from a pelvic bone. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

The invention described below generally relates to a tool and method being used in the process of hip cup replacement. To better understand the process with which the invention is used, below is a brief summary of the complete process of a hip cup replacement procedure using hip cup replacement devices in accordance with embodiments of the present invention.

The inside and outside diameters of the prosthetic hip cup to be removed are measured. A blade size is chosen to correspond to an outside diameter of the cup. A spherical head size is next chosen based on the inside diameter of the cup liner. The spherical head corresponding to the cup size is then installed onto a shaft configured with a short, starter blade, which begins the hip cup removal process. The starter blade, which is shorter and stiffer than a finishing blade (described below), is used around the top rim of the prosthetic hip cup to remove denser bone. The head is then seated into the old prosthetic hip cup liner. A mallet may be used to strike an impaction platform on the end of the shaft to help drive the blade into the pelvic bone. The shaft may then be pivoted and/or rotated to make an orbital cut around the old prosthetic hip cup. A handle positioned near the end of the shaft allows for easier rotation of the instrument.

Once the starter blade has removed the outer bone around the old prosthetic hip cup, the head may be removed from the starter blade shaft and installed on a finishing device consisting of a shaft having a finishing blade coupled thereto. The longer, thinner finish blade is used for deeper cutting around the dome of the old prosthetic hip cup. The shaft is pivoted and/or rotated is the same manner as the starter blade device until the finishing blade removes the bone around the old prosthetic hip cup. The old prosthetic hip cup may now be removed from the hip so that a new one can be inserted.

Figure 1:
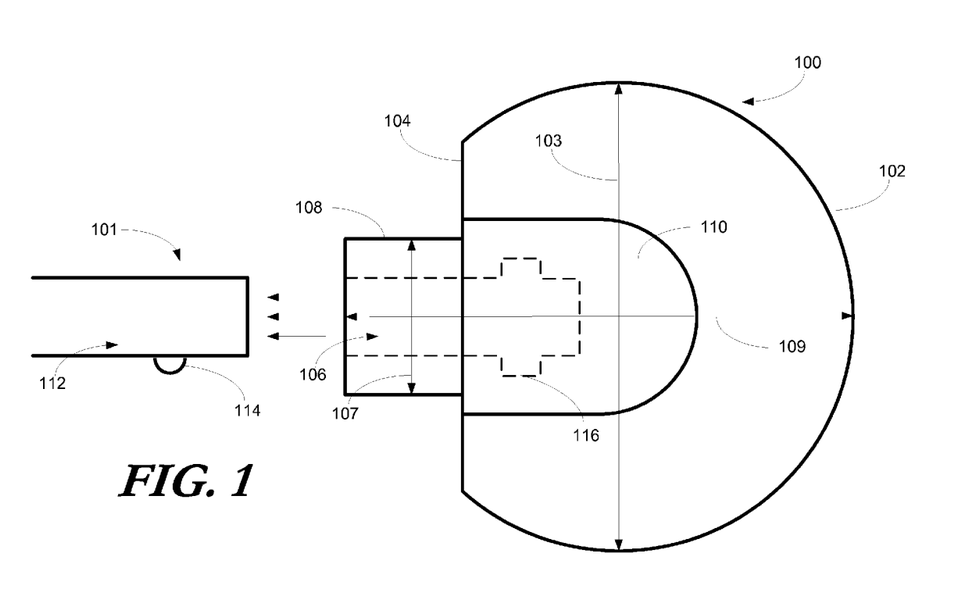
FIG. 1 illustrates one embodiment of a detachable head configured for selective attachment to a hip cup extraction apparatus in accordance with the invention.

Turning now to FIG. 1, illustrated therein is one embodiment of a head 100 configured for selective attachment to a hip cup extraction apparatus 101. In one embodiment, the head 100 may be manufactured from a rigid, durable material such as stainless steel. In another embodiment, the head 100 may be manufactured from a plastic or polymer, such as acetal resin plastic. It will be clear to those of ordinary skill in the art having the benefit of this disclosure that the head 100 may be manufactured from other rigid materials such as ceramics or other metals, plastics or polymers.

The head 100 comprises a semispherical section 102 which terminates in a substantially planar surface 104. As used herein, the term "semispherical" does not necessarily mean hemispherical. For the purpose of this invention, semispherical is defined as being a range of shapes that may be less than half a sphere, or may be greater than half a sphere. In one embodiment, the semispherical section 102 of the head 100 has a spherical section diameter 103 of between 39 millimeters and 60 millimeters.

The head 100 further comprises a hip cup extraction apparatus aperture 106 which may be disposed centrally along the substantially planar surface 104. When the head 100 is attached to the hip cup extraction apparatus 101, a shaft the hip cup extraction apparatus 101 fits inside of the hip cup extraction apparatus aperture 106. In one embodiment, the hip cup extraction apparatus aperture 106 has an aperture diameter 107 of between 7 millimeters and 12 millimeters. Experimental testing has shown that an aperture diameter 107 is between 9.525 millimeters and 9.551 millimeters works well in practice.

In one embodiment, the head 100 further comprises a cylindrical détente 116 disposed about the hip cup extraction apparatus aperture 106. Experimental testing has shown that a cylindrical détente 116 having a diameter of between 11.45 millimeters and 11.71 millimeters so as to accommodate a hip cup extraction apparatus 101 having a shaft 112 with a diameter of between 10.87 millimeters and 10.97 millimeters is effective in the removal of most commonly available hip cups. As illustrated in the exemplary embodiment of FIG. 1, the cylindrical détente 116 may be used to hold a spring loaded latching member 114 connected to the hip cup extraction apparatus 101 to enable the hip cup extraction apparatus 101 to latch on to the head 100 when then head 100 is attached to the hip cup extraction apparatus 101.

In one embodiment, the head 100 further comprises a retaining sleeve 108, which projects distally from the substantially planar surface 104 about the hip cup extraction apparatus aperture 106. The retaining sleeve 108 projects distally from the substantially planar surface 104 by at least 9 millimeters. The retaining sleeve 108 may be used to increase a head distal length 109. Increasing the head distal length 109 may increase the length of the hip cup extraction apparatus aperture and thus increase the length of the hip cup extraction apparatus 101 that is inside of the hip cup extraction apparatus aperture 106, thereby increasing the mechanical stability between the head 100 and the shaft 112.

Figure 2:
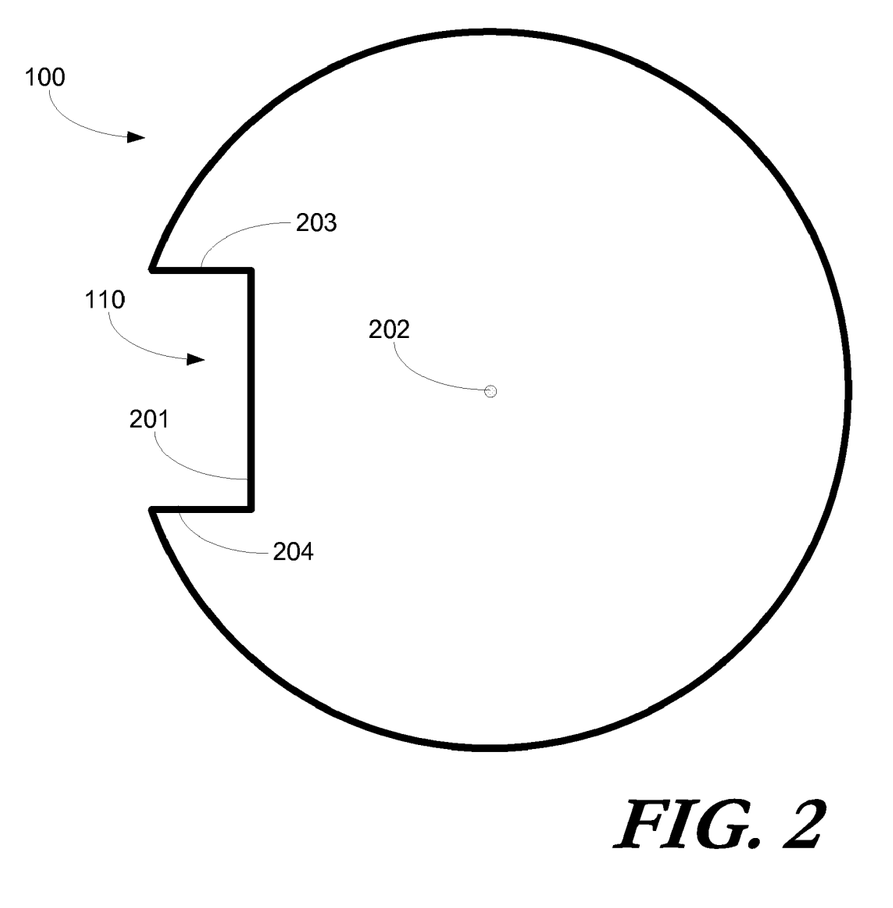
FIG. 2 illustrates a top plan view of a detachable head in accordance with one embodiment of the invention.

Turning briefly to FIG. 2, illustrated therein is a top plan view of the head 100. As can be seen from this view, the head 100 in one embodiment further comprises a three sided void 110 disposed along the semispherical section 102. The three sided void comprises a first side 201, a second side 203, and a third side 204. In one embodiment, the first side 201 may have a length of between 7 millimeters and 12 millimeters. The first side 201 may, alternatively, be less than 18 millimeters (measured radially) from a center 202 of the head 100. As will be seen below, the three sided void 110 allows the head 100 to be attached to a hip cup extraction apparatus 101 that has a blade coupled thereto without any mechanical interference.

Figure 3:
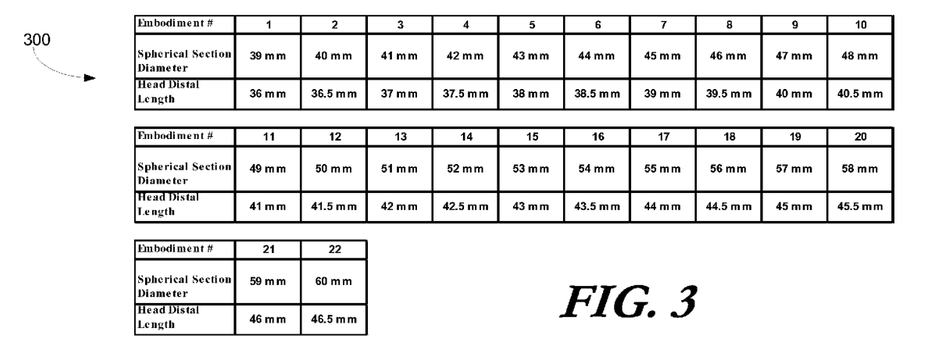
FIG. 3 illustrates a table showing various dimensions of a detachable head suitable for use with a hip cup extraction apparatus in accordance with embodiments of the invention.

Turning now to FIG. 3, illustrated therein is a table 300 showing various dimensions of a head (100) suitable for use with embodiments of the invention. Moreover, the table illustrates a plurality of paired values of spherical section diameters (103) and head distal lengths (109). Note that these values are meant to be exemplary only. It will be clear to those of ordinary skill in the art having the benefit of this disclosure that the spherical section diameter 103 and the head distal length 109 are not limited to just the respective pairings as shown in the table 300. Other embodiments, as dictated by the hip cup size to be removed by the invention, can equally be used. Additionally, it will be clear that the dimensions of the spherical section diameter (103) and the head distal length (109) are not limited to the integer values between their respective maximum and minimum values as shown in table 300.

Figure 4:
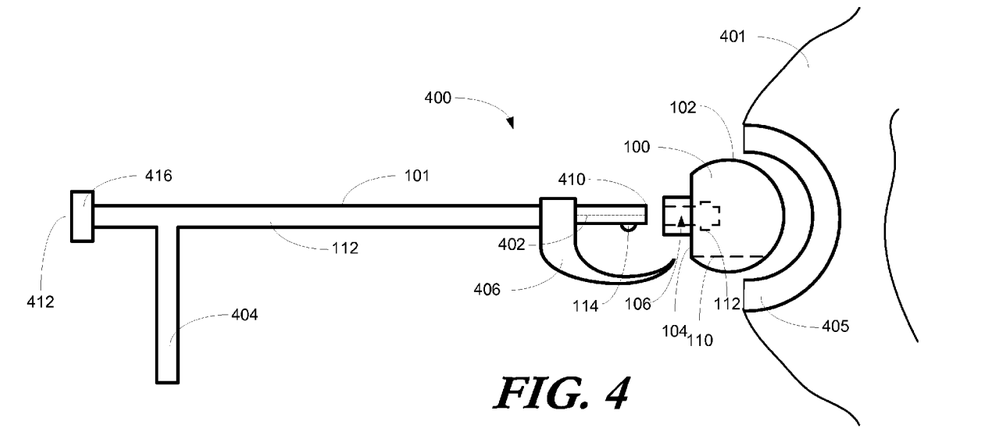
FIG. 4 illustrates one embodiment of the hip cup extraction device in accordance with the invention.

Now turning to FIG. 4, illustrated therein is one embodiment of the hip cup extraction device 400. The hip cup extraction device 400 may be used for removing a hip cup 405 from a pelvic bone 401. The hip cup extraction device 400 comprises a hip cup extraction apparatus 101 coupled to a head 100. The hip cup extraction apparatus 101 comprises a shaft 112 to which the head 100 may be selectively attached. In one embodiment, the shaft 112 has a length of at least 275 millimeters. The shaft 112 is preferably manufactured from a rigid material such as metal. Those with ordinary skill in the art having benefit of this disclosure will appreciate that the shaft may be manufactured from other rigid materials, such as plastics, polymers, and ceramics. The shaft 112 includes a first end 410 and a second, distal end 414.

The hip cup extraction apparatus 101 includes a handle 404 that projects outward from the shaft 402. In one embodiment, the handle 404 is disposed distally from the first end 410, toward the second end 412 of the shaft 112. The hip cup extraction apparatus 101 may further include an impaction platform 416 disposed at, or near, the second end 412 of the shaft 112. An impaction device, such as a hammer or mallet, may be used to hit the impaction platform 416 to drive the blade 406 into the pelvic bone to begin the cutting process.

The hip cup extraction apparatus 101 has a semicircular cutting blade 406 affixed thereto. The semicircular cutting blade 406 projects outwardly from the shaft 112. In one embodiment, the semicircular cutting blade 406 may terminate between 17 millimeters and 20 millimeters from a radial center of the shaft 112. Those with ordinary skill in the art having the benefit of this disclosure will appreciate that the semicircular cutting blade 406 may be manufactured in shapes and sizes other than that shown in FIG. 4. For example, the semicircular cutting blade 406 may be either a starter blade or a finishing blade. Additionally, the semicircular cutting blade 406 may take alternate shapes as dictated by the hip cup to be removed.

To retain the head 100 to the hip cup extraction apparatus 101, a latching device such as a spring loaded latching member 408, may be employed. The spring loaded latching member 408 is coupled to the shaft 112 between the semicircular cutting blade 406 and the first end of the shaft 402. In one embodiment, the spring loaded latching member 408 includes a circular void in the shaft 112, a metal ball bearing, and a spring. The diameter of the metal ball bearing is greater than an opening in the circular void. When the ball bearing is loaded against inner side of the circular void by the spring, part of the ball bearing protrudes through the circular void and extends outward from the shaft. When sufficient pressure is exerted against the spring loaded latching member 408, the ball bearing may retract into the shaft 112. It will be clear to those of ordinary skill in the art having the benefit of this disclosure that other latching mechanisms may also be used, including lever assemblies, snaps, and other similar devices.

The head 100 may be selectively attached to the hip cup extraction apparatus 101 so as to permit heads of different diameters to be used with the same hip cup extraction apparatus. The first end 410 of the shaft slides into the hip cup extraction apparatus aperture 106. As the head 100 slides onto the hip cup extraction apparatus 101, the tip 418 of the semicircular cutting blade 406 passes through the three sided void 110 so as to allow the head 100 to pass completely onto the hip cup extraction apparatus 101 without any mechanical interference. When the hip cup extraction apparatus aperture 106 passes over the spring loaded latching member 408, the spring loaded latching member 408 is depressed. Once the spring loaded latching member 408 reaches the cylindrical détente 116, the spring loaded latching member 408 extends into the cylindrical détente 116, thereby latching the head 100 to the shaft.

Figure 5:
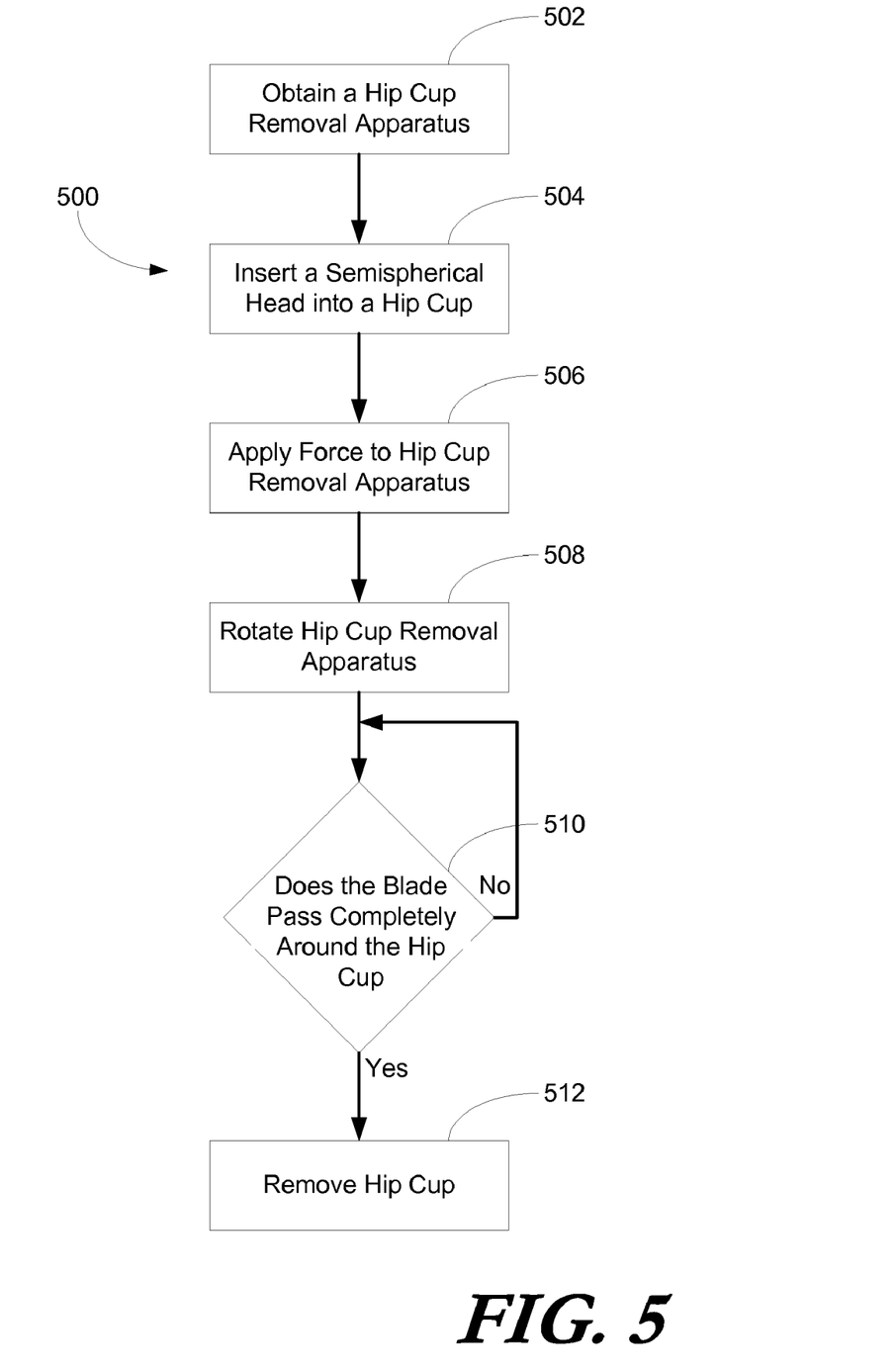
FIG. 5 illustrates one embodiment of a method for removing a prosthetic hip cup from a pelvic bone using a hip cup extraction device in accordance with the invention.

Turning now to FIG. 5, illustrated therein is one embodiment of a method 500 for removing a prosthetic hip cup from a pelvic bone. At step 502, a hip cup removal apparatus is provided. In one embodiment, the hip cup removal apparatus comprises a shaft, a semicircular cutting blade, a selective detachable, semispherical head, and a three sided void disposed along the semispherical head. At step 504, the semispherical head is inserted into a cup section of the prosthetic hip cup. At step 506, an optional impaction force may be applied to the hip cup removal apparatus to initiate a cutting action by the semicircular blade around the hip cup.

The hip cup removal apparatus is rotated, at step 508, such that the semicircular cutting blade passes about the hip cup. At step 510, the hip cup removal apparatus is rotated until the hip cup can be removed at step 512. In one embodiment of the method 500, the hip cup removal apparatus may be pivoted along an axis such that the semicircular cutting blade may pass completely about the hip cup. In a further embodiment of the method 500, a plurality of semicircular cutting blades—including a starter blade and a finishing blade—may be used in removing the hip cup.

Figure 6:
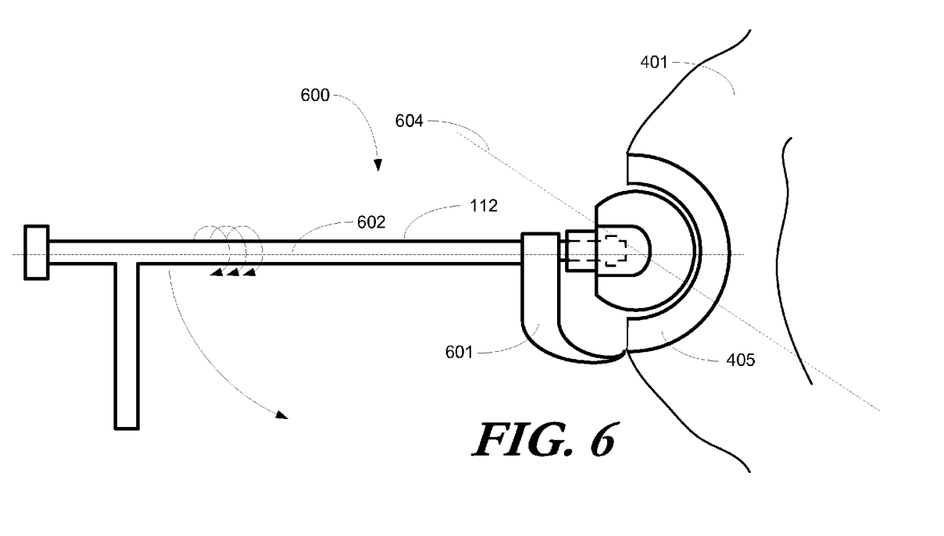
FIG. 6 illustrates a hip cup extraction device in accordance with embodiments of the invention.

Turning now to FIG. 6, illustrated therein is one embodiment of a hip cup extraction device 600 comprising a head 100 coupled to a shaft 112, where the head 100 has been inserted into a hip cup 405 contained in a pelvic bone 401. In the embodiment of FIG. 6, the hip cup extraction device 600 is configured with a starter blade 601 that may be used to cut around the outer rim of the hip cup 405 in order to remove the denser bone of the pelvic bone 401. The hip cup extraction device 600 may be rotated about a first axis 602 and pivoted about a second axis 604 in such a way that the starter blade 601 cuts around hip cup 405.

Figure 7:
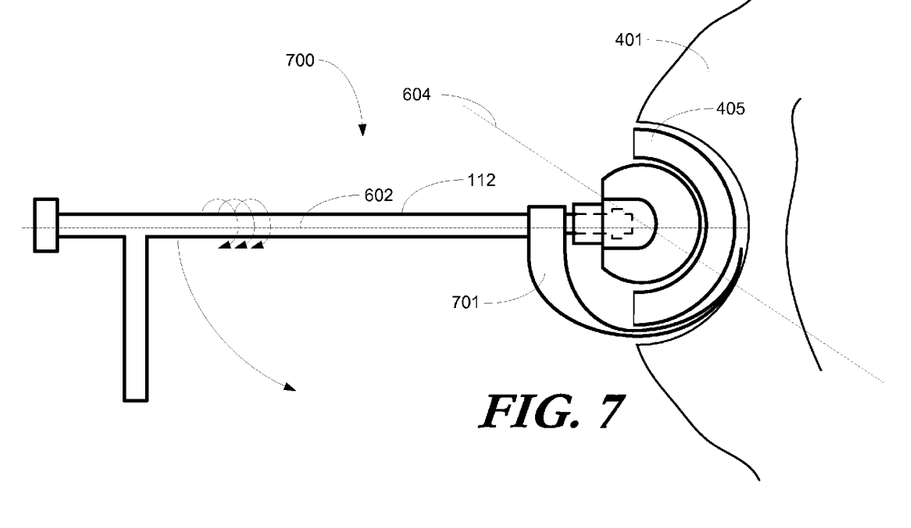
FIG. 7 illustrates a hip cup extraction device in accordance with embodiments of the invention.

Turning now to FIG. 7, illustrated therein is another embodiment of a hip cup extraction device 700 comprising a head 100 coupled to a shaft 112, where the head 100 has been inserted into a hip cup 405 contained in a pelvic bone 401. In the embodiment of FIG. 7, the hip cup extraction device 700 is fitted with a finishing blade 701 that may be used to cut around the inner surface of the hip cup 405 to complete the bone removal process. The hip cup extraction device 700 may be rotated about a first axis 702 and pivoted about a second axis 704 in such a way that the finishing blade 701 cuts around hip cup 405.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention.

What is claimed is:

1. A head configured for selective attachment to a hip cup extraction apparatus having a shaft and a cutting blade extending outwardly from a side of the shaft, the head comprising:
   a semispherical section terminating in a substantially planar surface, the semispherical section having a spherical section diameter of between 39 and 60 millimeters;
   a hip cup extraction apparatus aperture disposed centrally along the substantially planar surface;
   a retaining sleeve projecting distally from the substantially planar surface about the hip cup extraction apparatus aperture configured to receive an end of the shaft; and
   a three sided void disposed along the semispherical section;
   wherein the three sided void is configured such that when the head is being coupled to the shaft, a tip of the cutting blade may pass through the three sided void without mechanical interference.

2. The head of claim 1, wherein the head is manufactured from one of stainless steel or acetal resin plastic.

3. The head of claim 1, wherein the hip cup extraction apparatus aperture has an aperture diameter of between 12 and 18 millimeters.

4. The head of claim 3, wherein the aperture diameter of the hip cup extraction apparatus aperture is between 15.784 and 16.002 millimeters.

5. The head of claim 1, wherein the three sided void is characterized by a width of between 7 and 12 millimeters.

6. The head of claim 1, wherein the head further comprises a cylindrical détente disposed about the hip cup extraction apparatus aperture.

7. The head of claim 6, wherein the cylindrical détente has a diameter of between 11.296 and 11.557 millimeters.

8. The head of claim 1, wherein the retaining sleeve projects distally from the substantially planar surface by at least 9 millimeters.

9. The head of claim 1, wherein a first side of the three sided void is less than 18 millimeters from a center of the head.

10. A cutting apparatus for removing a hip cup from a pelvic bone, comprising:
- a shaft having a length of at least 275 millimeters;
- a handle extending distally from the shaft;
- a semicircular cutting blade coupled to the shaft, wherein the semicircular cutting blade projects outwardly from a side of the shaft;
- a spring loaded latching member coupled to the shaft between the semicircular cutting blade and a first end of the shaft; and
- a head comprising a semispherical section terminating in a substantially planar surface, and a three sided void disposed along the semispherical section;
- wherein the three sided void is configured such that when the head is being coupled to the first end of the shaft, a tip of the semicircular blade may pass through the three sided void.

11. The cutting apparatus of claim 10, wherein the handle is disposed at a distal end of the shaft relative to the head.

12. The cutting apparatus of claim 10, further comprising an impaction platform disposed at a second end of the shaft.

13. The cutting apparatus of claim 10, wherein the semicircular cutting blade terminates between 17 and 20 millimeters from a radial center of the shaft.

14. The cutting apparatus of claim 10, wherein the shaft is manufactured from metal.

15. The cutting apparatus of claim 10, wherein the semispherical section of the head has a spherical section diameter of between 39 and 60 millimeters.

16. The cutting apparatus of claim 10, wherein one side of the three sided void is within 17.12 millimeters of a center of the shaft when measured along a line normal to the one side.

17. The cutting apparatus of claim 16, wherein the three sided void is characterized by a width of between 7 and 12 millimeters.

18. The cutting apparatus of claim 10, wherein the head is selectively detachable.

19. The cutting apparatus of claim 10, wherein at least two sides of the three sided void are oriented parallel with the shaft.

* * * * *